United States Patent
Furze et al.

(10) Patent No.: US 7,771,776 B2
(45) Date of Patent: Aug. 10, 2010

(54) APPARATUS AND METHOD FOR INSPECTING GOLF BALLS USING SPECTRAL ANALYSIS

(75) Inventors: Paul A. Furze, Tiverton, RI (US); Matthew F. Hogge, Plymouth, MA (US); Brian P. St. Aubin, South Dartmouth, MA (US)

(73) Assignee: Acushnet Company, Fairhaven, MA (US)

( * ) Notice: Subject to any disclaimer, the term of this patent is extended or adjusted under 35 U.S.C. 154(b) by 1084 days.

(21) Appl. No.: 11/230,185

(22) Filed: Sep. 19, 2005

(65) Prior Publication Data

US 2006/0012790 A1 Jan. 19, 2006

Related U.S. Application Data

(63) Continuation-in-part of application No. 10/867,495, filed on Jun. 14, 2004.

(51) Int. Cl.
*B05D 3/00* (2006.01)
(52) U.S. Cl. .................................. 427/9; 427/8; 427/10
(58) Field of Classification Search ................ 427/8–10
See application file for complete search history.

(56) References Cited

U.S. PATENT DOCUMENTS

| | | | | |
|---|---|---|---|---|
| 4,641,972 | A | | 2/1987 | Halioua et al. .............. 356/376 |
| 5,506,004 | A | * | 4/1996 | Maruoka et al. ............. 427/425 |
| 5,777,244 | A | | 7/1998 | Kumagai et al. |
| 5,938,545 | A | | 8/1999 | Cooper et al. ............... 473/407 |
| 5,960,098 | A | | 9/1999 | Tao ............................. 382/110 |
| 6,031,933 | A | * | 2/2000 | Kumagai ..................... 382/141 |
| 6,271,520 | B1 | | 8/2001 | Tao et al. .................... 250/330 |
| 6,462,303 | B1 | | 10/2002 | Brown ................... 219/121.69 |
| 6,462,812 | B1 | | 10/2002 | Heene et al. ............. 356/237.1 |
| 6,484,121 | B1 | | 11/2002 | Filev et al. ................... 702/170 |
| 6,495,833 | B1 | | 12/2002 | Alfano et al. ............. 250/341.8 |
| 6,532,066 | B1 | | 3/2003 | Filev et al. ............... 356/237.2 |
| 6,630,998 | B1 | * | 10/2003 | Welchman et al. .......... 356/394 |
| 2001/0012389 | A1 | * | 8/2001 | Welchman et al. .......... 382/141 |
| 2003/0090659 | A1 | * | 5/2003 | Welchman et al. .......... 356/394 |
| 2004/0022948 | A1 | | 2/2004 | Brown et al. ................. 427/314 |
| 2005/0200837 | A1 | * | 9/2005 | Mydlack et al. .......... 356/237.1 |

OTHER PUBLICATIONS

Agema Thermovision® 570, Advanced Test Equipment Rentals.
D Sight, Solutions for Advanced Manufacturing (SAM), Diffracto Ltd.

(Continued)

*Primary Examiner*—David Turocy
(74) *Attorney, Agent, or Firm*—Daniel W. Sullivan

(57) ABSTRACT

A method for inspecting golf balls is disclosed. An imager such as a camera captures a spectral image of the golf ball. The spectral image is captured line-by-line as the golf ball rotates. The lines are then packed together to form a three-dimensional spectral image of the golf ball showing full spectral information for every pixel. The resultant three-dimensional spectral image is then analyzed, such as using a pattern matching or threshold analysis tool. If a golf ball passes the inspection, it is permitted to advance in the processing. If the golf ball does not pass the inspection, it may be diverted. This inspection system is capable of detecting very subtle color differences, so the system is particularly applicable for use in inspecting primer coat coverage.

17 Claims, 4 Drawing Sheets

OTHER PUBLICATIONS

J.C. Martínez-Antón, H. Caníbal, J.A. Quiroga, E. Bernabeu, M. Álvaro Labajo, and V. Cortés Testillano, Enhancement of Surface Inspection by Moiré Interferometry Using Flexible Reference Gratings, Optics Express, Jun. 4, 2001, vol. 8, No. 12, pp. 649-654.

Maria E. Nadal and E. Amber Thompson, New Primary Standard for Specular Gloss Measurements, Journal of Coatings Technology, Dec. 2000, vol. 72, No. 911, pp. 61-66.

Maria E. Nadal and E. Amber Thompson, Nist Reference Goniophotometer for Specular Gloss Measurements, Journal of Coatings Technology, Jun. 2001, vol. 73, No. 917, pp. 73-80.

Moire Fringe Contouring, University of Glasgow, 2001.

Nikon Thermal Vision Laird-S270: Ultra-Compact Infrared (IR) CCD Camera Provides Advanced Features and Superb Image Quality, Nikon News.

R. Pezzoni, Laser-Shearography for Nondestructive Testing of Large Area Composite Helicopter Structures.

Tom Thompson, Charge-Coupled Device, Computer World.

Wayne Ruddock, Infrared Thermography vs The Visible, InfraredThermography.com.

Yoseph Bar-Cohen, Emerging NDE Technologies and Challenges at the Beginning of the $3^{rd}$ Millennium—Part I, Part II, Jet Propulsion Laboratory, NDT.net, Jan. 2000, vol. 5, No. 1.

* cited by examiner

APPARATUS AND METHOD FOR INSPECTING GOLF BALLS USING SPECTRAL ANALYSIS

CROSS-REFERENCE TO RELATED APPLICATION

The present application is a continuation-in-part of co-pending U.S. patent application Ser. No. 10/867,495 filed on Jun. 14, 2004.

FIELD OF THE INVENTION

This invention generally relates to visually inspecting golf balls and more specifically to visually inspecting golf balls using a spectral analysis system.

BACKGROUND OF THE INVENTION

The manufacture of golf balls typically involves a series of sequential processes performed at different processing stations, spatially separated one from another. Golf balls typically have at least a core and a dimpled cover formed over the core. The outer cover of the golf ball is formed with various materials, such as urethane elastomers, urea, balata, ionomers or any other appropriate materials. The cover surfaces are formed with dimples of various numbers, sizes and patterns, which improve flight distance, control and stability. The golf ball cover generally contains a white or other colored concentrate, or is painted. The outer surface of the ball covers usually have the manufacturers indicia painted thereon, as well as an application of a paint or clear coat for good appearance, improving flight distance and protecting of the indicia imprinted thereon.

Freshly coated golf balls are transported from a clear coat spray paint booth to a separate drying station at a remote location. Additional printing, such as a logo, may be applied over the cured clear coat.

Each process must be carefully monitored for quality assurance purposes. Inspections based on predetermined control criteria are performed to achieve a desired production quality. The manufacturer can manually inspect the entire lot if a given number of defective balls are found therein. Moreover, if a major defect, such as a gross cosmetic defect or a defect affecting performance or durability, is found, the manufacturer may choose to shut down the entire system.

Since automated production is faster and less expensive, each of the above processes can be performed at a separate automated processing station functioning at optimal efficiency and speed, so that the overall production rate is maintained at the desired high level. For instance, pad-printing apparatus preferably includes an array of print-pads arranged to apply a production print sequentially on various locations on the surface of the golf ball, with the golf ball being indexed before being passed to the next print-pad. Also, the clear coating process preferably is performed by an automated spray painting technique utilizing a spray paint booth with one or more spray paint guns. A quick drying clear coat paint having a catalyzing agent may be used to reduce the usual clear coat drying time of about ten hours to about one hour or less.

On the other hand, automation of the manufacturing process may cause various manufacturing defects. For example, automated pad-printing equipment may leave smudges from excess ink carried by the printing pad. Vibration or improper set-up, such as improper positioning or accidental switching of the paint supply hoses cutting off paint supply to the spray guns, causes defective coating on golf balls. Moreover, the clear coat paint may periodically clog the spray booth filter, interfering with proper spraying of paint.

While clear coat spray painting operation utilizing catalyzation can significantly reduce the curing time, catalyzation can also occur in the spray booth, resulting in a thick brittle coating on the spray booth filter and increasing the probability of spray paint malfunctions. Clogging of spray guns and gelling of the clear coat during application result in inadequate clear coating of the golf ball. Moreover, transferring the freshly coated golf ball to the curing station before inspection does not alert the operator to attend to unacceptable spray painting apparatus conditions until the end of the curing process. Thus, to maintain high production rates, it is necessary to identify the defective products early in the treatment process.

Given the quality control necessary to meet production standards and the high production rates of golf ball manufacturing plants, actions to correct a malfunction in the automated processing equipment should be taken as soon as possible. Accordingly, there is a need for speedy and efficient inspection of golf balls so that any manufacturing problem may be corrected early to reduce further production of defective balls.

A variety of automated inspection systems and methods are used in quality control of automated processing stations, such as for coating, finishing, or otherwise affecting the surface appearance of products. Most of the known automated inspection systems employ vision cameras to capture an image of the products. The products to be inspected are typically illuminated to allow the cameras to see the entire products, e.g., dimpled golf balls are illuminated to prevent shadows from forming in the dimples. U.S. Publ. App. No. 2001/0012389 discloses another golf ball inspection system using a custom lighting system. U.S. Pat. No. 5,777,244 discloses an elaborate system to illuminate golf balls. U.S. Pat. No. 6,462,812 discloses an inspection utilizing a plurality of charge-coupled device (CCD) cameras to inspect indicia on golf balls. CCD is an integrated circuit that converts light to electrical signals. A digital camera using CCD can comprise millions of pixels. U.S. Pat. No. 5,960,098 discloses a vision system for inspecting fruits. This system also utilizes CCD cameras, albeit with an infrared lens, to capture the images of fruits.

At least one vision inspection system employs infrared cameras for inspection. U.S. Pat. No. 6,271,520 discloses a system for inspecting fruits. This system uses a first camera in the near IR range and a second camera in the mid IR range to capture images of the products to be inspected. The background information is removed and the two images are subtracted leaving the defects. Another drawback of this system is that at least a portion of the exterior surface of the products to be inspected must be raised about 5° C. to 15° C. higher than ambient conditions.

U.S. Pat. No. 6,630,998 discloses light-emitting diodes mounted over the golf balls to be inspected to provide constant and even light sources. In addition to using non-ambient light sources for even lighting, the '998 patent discloses the use of ultraviolet lighting in order to detect the presence of a substance, such as a coating, applied to the surface of a golf ball. Images of the golf ball are captured by a detecting apparatus and then analyzed using discrete element detecting algorithm and industry standard blob analysis. Standard blob analysis tools count the number of discrete elements in the viewing area. This technique uses an algorithm to create a boundary outline around each discrete element being inspected. The boundary is broken down, such as into small line segments and arcs, to create a geometric representation which may be modified based on a best fit algorithm to match the object being inspected to a reference image. The algorithm then searches for breaks or significant changes in contour along the boundary, missing ink inside each boundary, and excess ink, marks, smudges, or doctor blade marks outside each boundary. Additionally, the boundary detection algorithm may calculate the relative positions of pairs of indicia, such as a logo and a number, to assure correct positioning. This is done by comparing the pattern detected in an inspection image with a predefined reference pattern. In a vision inspection system, the discrete element typically is identified as a continuous area of dark pixels exceeding a specified gray scale value without a break.

However, the systems of the prior art often have difficulties in determining the coverage of the primer layer underneath the outer painted layer on urethane covered balls. When a golf ball has poor primer coverage, small dots of the urethane cover material show through the paint and slightly change the color of the ball. Standard color cameras have difficulties detecting this minor change. While the color variance is noticeable with the eye, the eye will also have difficulties in seeing the slight color change, especially at manufacturing speeds. Therefore, a need exists in the art for an automated system that can inspect a golf ball for the subtle color changes, such as those that indicate poor prime coat coverage.

SUMMARY OF THE INVENTION

One aspect of the present invention is directed to a method for inspecting a golf ball in an automated manufacturing system comprising the steps of: (i) aligning the golf ball with a spectral imager, (ii) obtaining a spectral image of at least a portion of the golf ball, (iii) analyzing the spectral image, and (iv) acting on the golf ball.

Another aspect of the present invention is directed to an imager for inspecting an object having a plurality of fiber optic elements at least partially surrounding the object. At least one of the fiber optic elements is a sensor and at least one of the fiber optic elements is an illuminator. A controller is also connected to the plurality of fiber optic elements.

BRIEF DESCRIPTION OF THE DRAWINGS

In the accompanying drawings, which form a part of the specification and are to be read in conjunction therewith and in which like reference numerals are used to indicate like parts in the various views.

DETAILED DESCRIPTION OF THE PREFERRED EMBODIMENTS

Figure 1:
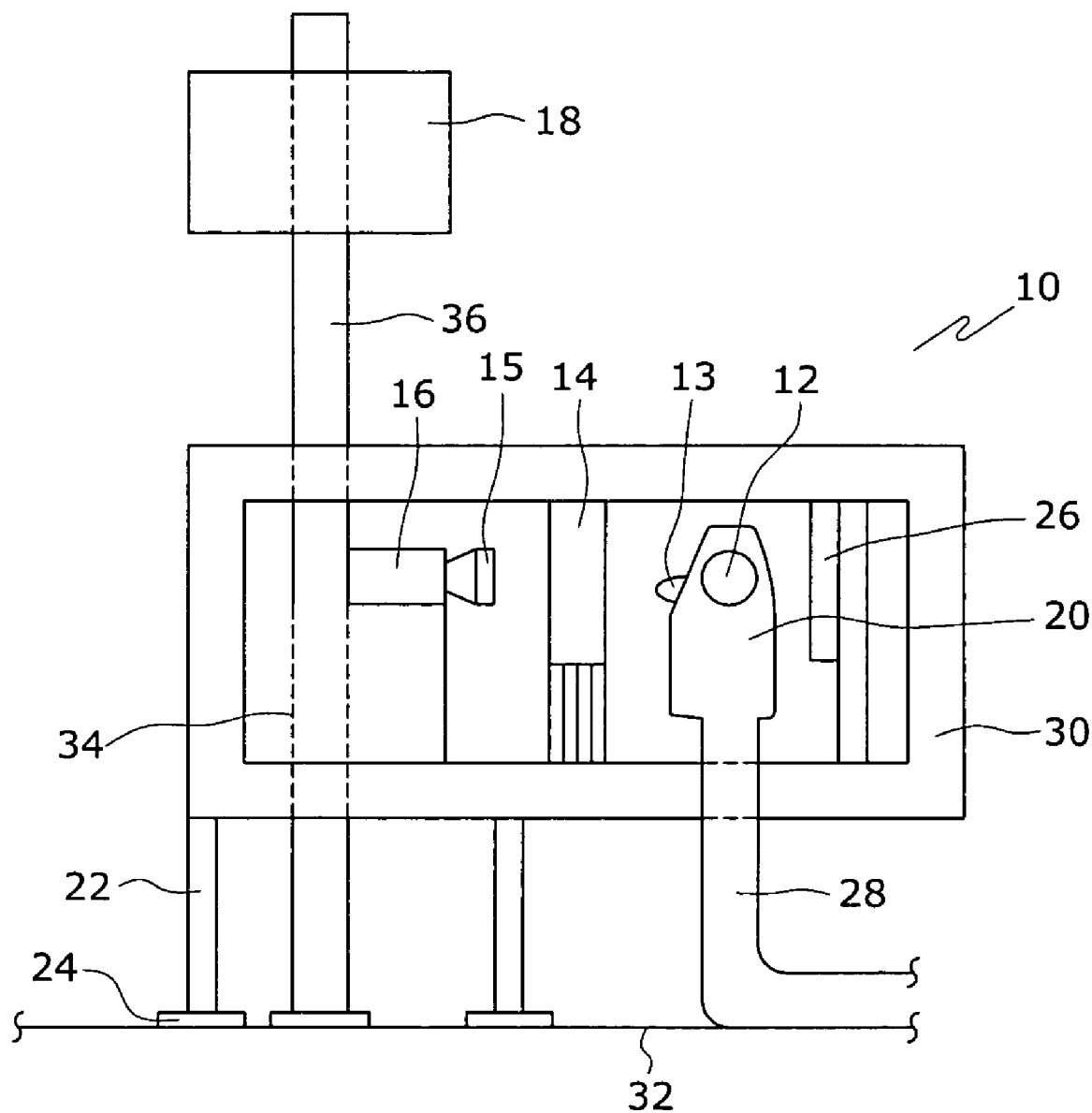
FIG. 1 is a schematic front view of a vision inspection system according to the present invention.

As shown schematically in FIG. 1, the present invention relates to the modification of or addition to one or more automated game ball processing stations of a ball manufacturing process to include an automated inspection system 10. Automated inspection system 10 permits continuous, objective inspection of all of the balls being processed by automated processing apparatus without interrupting or slowing down or otherwise interfering with processing and production of the balls. Automated inspection system 10 not only provides important information for use in quality control, but also permits further automated actions to be taken with respect to the balls being processed, as described herein. Thus, in accordance with the principles of the present invention, the ball manufacturing process is further streamlined and production speed and efficiency are increased.

In a preferred manufacturing process according to the present invention, the automated processing station provides a surface treatment for a golf ball 12 during the manufacture of golf balls. For example, processing apparatus may treat the surface of golf ball 12 by applying a substance, such as primer, thereon. Preferably, an optical brightener or a slight colorant such as a colorant in the red or blue portion of the spectrum is also included in the surface treatment, in order to facilitate the vision inspection process. Alternatively, as the primer coat is often pure white, a slight coloring additive may be added to the material of the outer, unpainted cover of golf ball 12, such as a red or blue tinge, in order to better differentiate between primed and unprimed portions of the surface of golf ball 12. After the primer coat is applied, golf ball 12 is preferably inspected to assure optimal primer coverage over the surface of golf ball 12 before a second treatment, such as a layer of paint of any color such as white, is applied. As such, after treatment, golf ball 12 is transferred, preferably by an automated transferring mechanism, directly to automated inspection system 10 which is positioned downstream along the production line.

Figure 2:
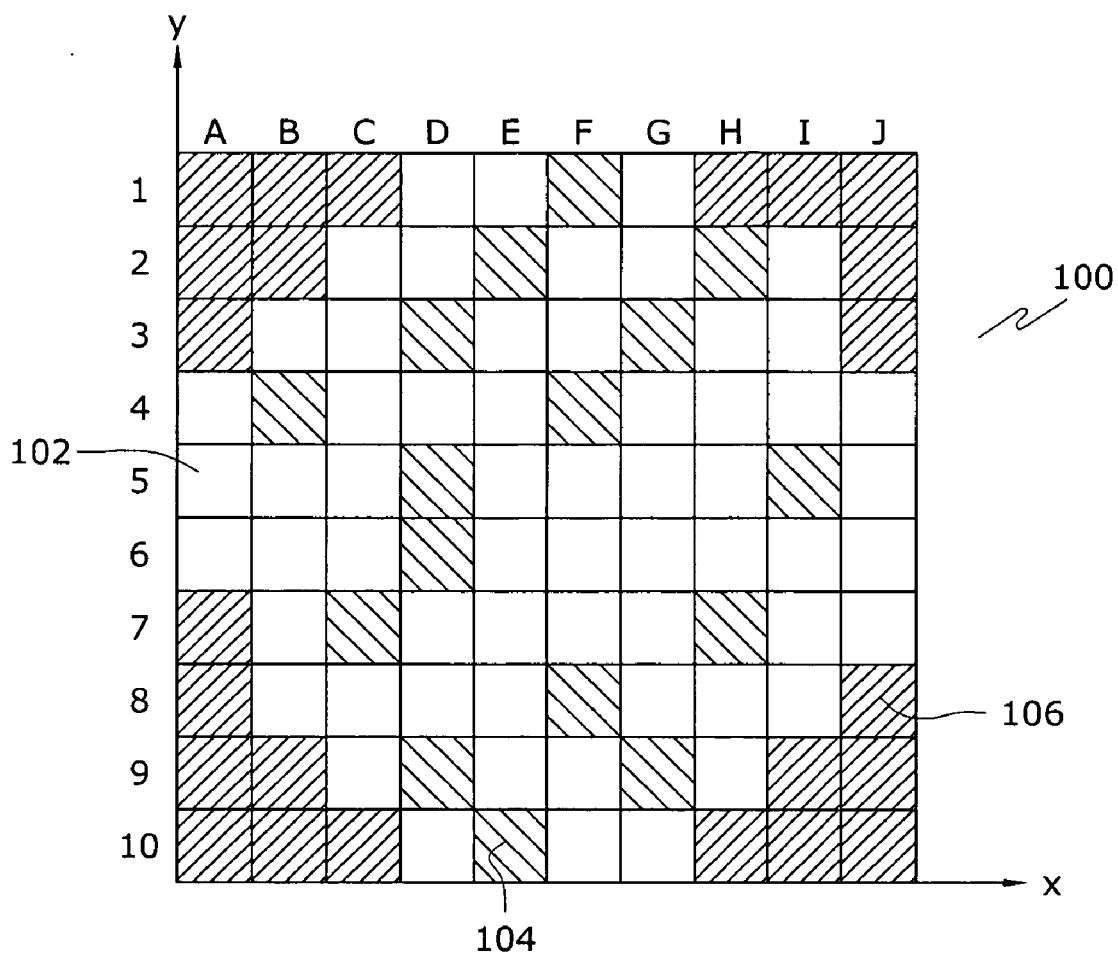
FIG. 2 is a schematic view of a low-pixel digital image of a golf ball.

Referring to FIGS. 1 and 2, in a preferred embodiment, automated inspection system 10 comprises an imager 16 and an automated analyzer 18 linked together preferably via an electronic link that runs through or on a vertical support 36. Analyzer 18 determines whether or not golf ball 12 has been appropriately coated, preferably using spectral analysis to detect subtle differences in the color of the surface of golf ball 12 due to uneven primer coverage. Imager 16 is mounted on a riser 34 that positions imager 16 on a line-of-sight relationship with golf ball 12 in a ball holder 20. Ball holder 20 is preferably a tube through which golf ball 12 travels. The side of ball holder 20 facing imager 16 is preferably removed so as to provide imager 16 with a clear view of golf ball 12. Preferably, ball holder 20 includes a turning mechanism (not shown) so that imager 16 may capture images of the whole of golf ball 12 without the need for moving imager 16.

Imager 16 is preferably a line-scanning spectral camera. Imager 16 is more preferably a camera that detects and records the spectral footprint of images in the visual range, such as a color or black and white camera mounted to a spectrograph. An appropriate spectral camera for use with the present invention is available from, among others, Redlake MASD, LLC of San Diego, Calif. Imager 16 either captures a digital image or captures an analog image and processes the analog image into a digital image for transmission to analyzer 18. The image captured may be either gray scale or in color.

Preferably, imager 16 captures a color image. In such a case, color for the digital or digitized images is produced by mixing primary colors using one of several color conventions such as RBG (Red-Green-Blue), CMYK (Cyan-Magenta-Yellow-Black). Using these color conventions, each pixel of the image is assigned a single color that is composed of smaller bits of primary colors. For example, using the RGB convention, red, green, and blue bits are combined to form various colors, such as white, where true white is a blend of red, green, and blue bits in equal parts. The precise shade of white may be altered by varying the relative percentages of the primary color bits, such as increasing the percentage of red bits. Of course, given the small size of each bit, the overall white color appears uniform. The number of bits per pixel is typically either 16 or 24. Colors may also be represented digitally in the color spectrum, or visible range of radiation, wherein each color has a unique range of wavelengths. For example, each primary color RBG has a unique spectral range. Any color, for example white, may be expressed as a combination of the RBG wavelengths.

In one embodiment, as shown in FIG. 1, imager 16 views and detects golf ball 12 and provides a detection signal, such as a spectral image of golf ball, into automated analyzer 18. Analyzer 18 receives the detection signal and uses the signal to perform various analysis tasks such as analysis of the signal, statistics processing, task scheduling, generation of reject signals or further control signals, and/or alarms. Analyzer 18 is preferably placed so that an operator has easy and quick access to both the analyzer 18, to determine any potential defects, and the production line, to identify and correct the cause of the defect.

Imager 16 preferably supplies high resolution images to analyzer 18. The physical resolving power is dependent on the field of view of imager 16 and distance from the ball surface. For instance, a one square inch field of view can be depicted by hundreds of thousands of pixels, each having a wide range of colors or shades of gray. Thus, differences in golf ball color or shading, such as caused by the application of a surface treatment such as a coating, ink or paint to the golf ball surface, may be detected electronically.

Preferably, imager 16 captures and transmits the spectral footprint of an image one line of pixels at a time. For example, as shown in FIG. 2, a digitized image 100 of a golf ball such as golf ball 12 is shown. Image 100 is composed of rows and columns of pixels, which are designated by numbers, 1-10, and letters, A-J, respectively, for the purposes of clarity for the discussion. Each pixel has a color, such as, for example, white, black, red, or blue. For ease of discussion, each pixel in image 100 has been assigned one of three colors: white 102 to represent an area of effective primer coverage, red 104 to represent an area of ineffective primer coverage, and black 106 to represent the background (if any). Image 100 is a simplified representative image only; in an actual image, each row typically contains approximately 640 pixels. Further, in an actual image, multiple colors and shades would be present.

Figure 3:
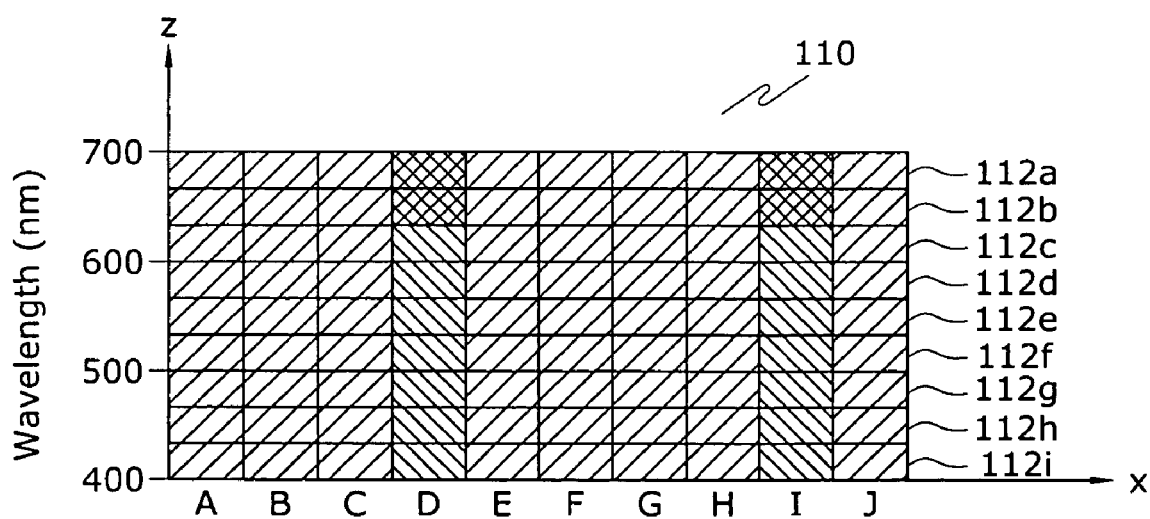
FIG. 3 is a schematic view of a single line of a spectral image of the golf ball of FIG. 2 as captured by a spectral camera according to the present invention.

As imager 16 is preferably a line-scanning spectral imager, a spectral image of a single row, such as row 5, is taken with each image capture. FIG. 3 shows a schematic spectral image 110 corresponding to row 5 from FIG. 2. In spectral image 110, the x-axis is distance along row 5 and the z-axis is the wavelength of a desired portion of the spectrum, such as the visible spectrum, in nanometers. As shown in FIG. 3, spectral image 110 ranges only from 400 nm, in the violet portion of the visible spectrum, to 700 nm, in the red portion of the visible spectrum. Those skilled in the art will recognize that the designated portion of the spectrum may be wider, such as ranging from the ultraviolet or to the infrared portion of the spectrum. Similarly, the designated portion of the spectrum may be narrower, such as only in the red portion, in order to more clearly focus on colors that may represent defects in surface treatment coverage.

In spectral image 110, each pixel is represented by a series of wavelength bands 112*a-i* extending along the x-axis showing the intensity at each wavelength on the z-axis from the reflection from golf ball 12. For example, pixel 5A is white, so each wavelength band 5A-112*a-i* shows a similar intensity. In other words, since white light is a mixture of all wavelengths of visible light, each wavelength band 112*a-i* is of equal intensity. In contrast, pixel 5D is red, so the red wavelength bands 5D-112*a*, 5D-112*b* show a high intensity while the remainder of the wavelength bands 5D-112*c-i* show a low or no intensity.

Spectral image 110 may also be captured in grayscale. In this case, each wavelength band 112*a-i* would contain information related to a brightness value of the pixel. For example, brightness is preferably separated into 255 units with 8 bit resolution on the gray scale, with 0 defining black regions and 255 defining pure white regions, although any gray scale resolution may be used. Each color of the visible spectrum correlates to a particular value on the gray scale continuum. Therefore, spectral image 110 may also show the intensity, or brightness, of each wavelength band in order to establish a spectral image in grayscale.

Figure 4:
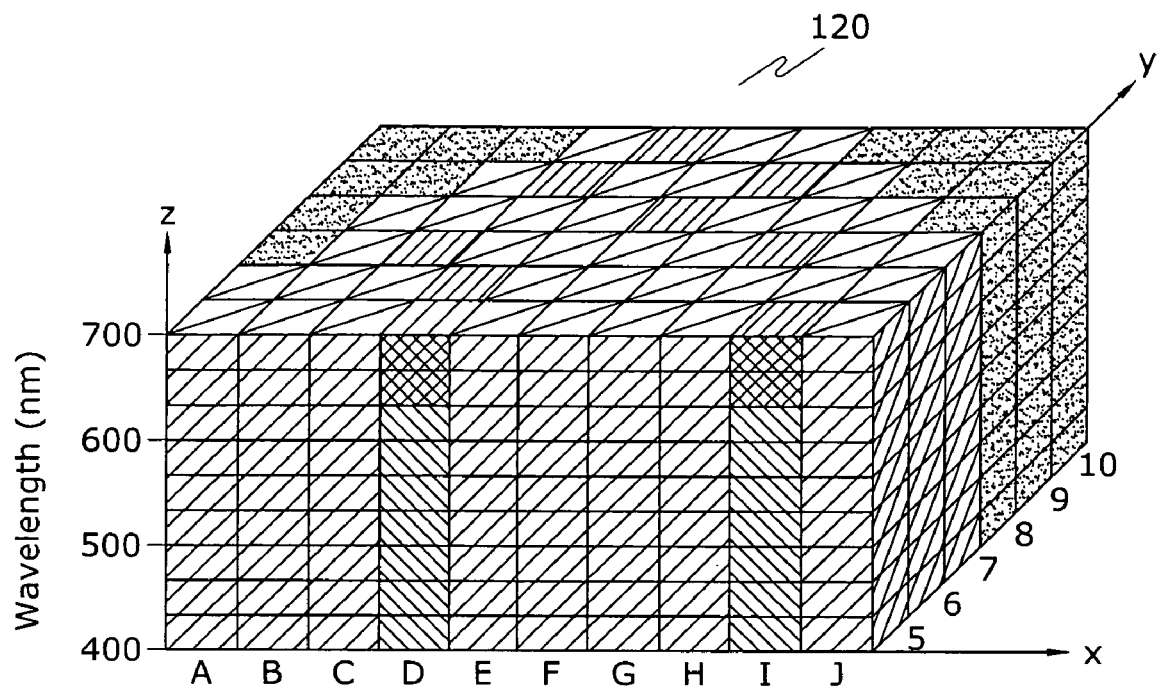
FIG. 4 is a schematic view of an amalgamated three-dimensional spectral image of the golf ball of FIG. 2.

This process of gathering a spectral image for each row 1-10, as illustrated in FIG. 2, is repeated until the entire object, such as golf ball 12, is represented. This is accomplished by spinning golf ball 12 at a known frequency of revolution and taking a large number of spectral images, for example 1000 images per revolution. The spectral images for each line are then packed together to form a three-dimensional image 120, a partial view of which is shown in FIG. 4, with the spectral images from rows 5-10 shown packed together. In other words, pixels located on rows 5-10 along columns A-J are now illustrated on the horizontal x- and y-axes, and the spectral footprint of each pixel, as expressed in nm wavelength, are illustrated on the vertical z-axis, thereby giving the spectral images a three-dimensional appearance. This process may be facilitated by including an encoder on the rotational axis of ball holder 20 (shown in FIG. 1). For example, the encoder may emit a pulse each time a point on golf ball 12 passes the encoder. This pulse can be used to signal a controller to refocus imager 16 on another line of golf ball 12. In other words, as golf ball 12 spins within ball holder 20, imager 16 initially captures images on a single line, for example row 1 of FIG. 2. When the encoder emits the pulse, imager 16 trains instead on the next line of the object, for example, row 2 of FIG. 2. In a preferred embodiment, imager 16 captures 600 lines to represent ball 12.

Once three-dimensional image 120 has been obtained, analyzer 18 then preferably performs additional analysis on the image. For example, the image obtained from system 10 may be compared with stock image taken from an acceptable reference or "master" ball. Analyzer 18 may compare the images using, for example, any of the known pattern matching algorithms. If the patterns match, then analyzer 18 can take any number of actions, such as sending a signal to the automated ball processing system to advance golf ball 12 to the next stage. If the patterns do not match, then analyzer 18 may signal the operator, divert golf ball 12 from the production line, send golf ball 12 to another station for reapplication of additional primer, or take other action. Alternatively, analyzer 18 may use a threshold analysis technique, such as detecting and counting the number of pixels with an overly red shift. If the threshold is breached, then analyzer 18 may, for example, divert golf ball 12 or take any of the actions described above with respect to pattern matching.

Figure 5:
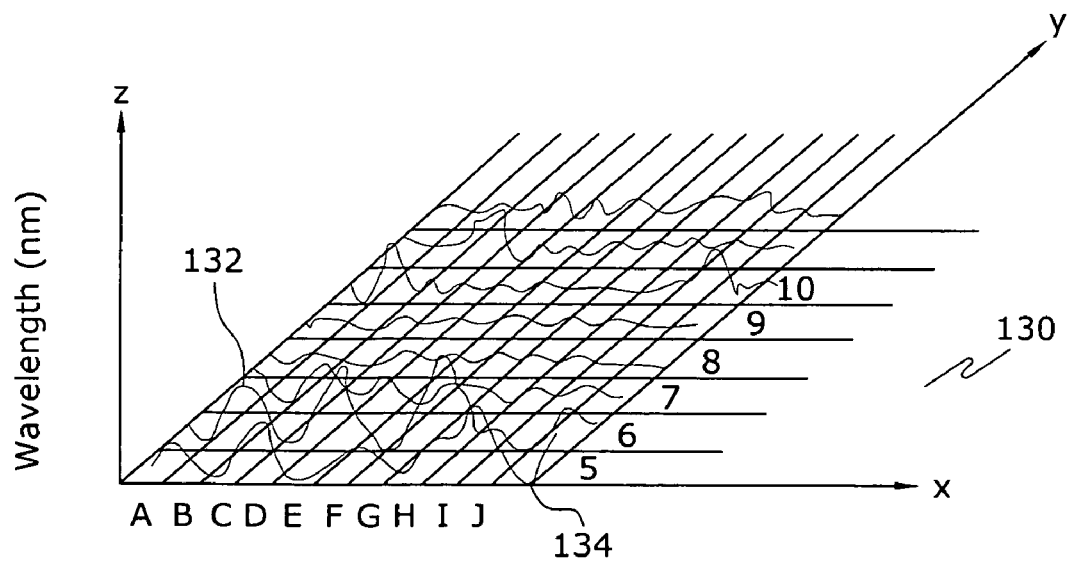
FIG. 5 is a schematic view of the topography of a portion of the spectral data represented in the three-dimensional spectral image in FIG. 4.

Alternatively, the spectral data gathered by imager 16 may be additionally processed prior to comparison with reference tables from the master ball. For example, the two-and three-dimensional spectral images 110, 120 as shown in FIGS. 3 and 4 show that golf ball 12 is mostly white with various red spots. In order to facilitate processing of this spectral data, the white portion of the data may be removed from three-dimensional image 120, such as by subtracting the numerical value for white, either in a color scheme or gray scale scheme, from three-dimensional image 120. This subtraction yields three-dimensional image 130, shown in FIG. 5, which is similar to a topographical map. In image 130, a series of graphical peaks 132 and troughs 134 represent the remaining spectral components after removal of the main color, such as white. In other embodiments, the color of the primer may be a color other than white, for example, when the final painted ball is to be a color other than white, such as yellow or blue. Image 130 may then be compared with a similar image from the master ball or simply analyzed to determine if too many peaks remain after subtraction of the desirable color.

One way in which color can be determined is by measuring the reflectance of the ball, Rb. Ball reflectance Rb is separated from the system response by taking, pixel by pixel, the ratio of each sample image to the white image. This method of measuring color also compensates for offset due to CCD dark current, lighting spatial non-uniformity across the scene line, and light source color temperature drift. As measuring reflectance provides a wavelength of the ball, a specific color or colors may be identified within a tolerance range.

A variety of inspection routines may be performed by analyzer 18, such as finding the center of the product, checking overall dimensions and contours, inspecting for contamination, and/or determining various characteristics of a surface treatment such as an application of a substance (e.g., primer, coating, ink or paint) to the surface of the golf ball. For example, after the colors or distribution of colors on a ball are identified, the location of the color on the ball from a reference point may be determined using any method known in the art, such as by using an edge finding tool or a histogram algorithm as described above. In this manner, balls having multiple colors, such as balls with graphics printed thereon, can be inspected for accuracy not only of color but of the placement of color. Because a variety of different aspects of the golf ball are inspected and analyzed, different areas on the surface of the golf ball must be inspected, and a variety of different, potentially overlapping, inspection routines are performed to provide the data necessary for the inspection analysis. The specific inspection routine performed on the golf ball is selected based on the process being inspected, as will be described in further detail below in connection with exemplary applications of the principles of the present invention.

As will be recognized by those in the art, spectral imaging may also be used to visually inspect a golf ball for a variety of quality control aspects, including paint coverage, effective logo application, and accuracy of color from batch to batch. Further, the inspection system may be used for objects other than golf balls, such as fruit, for which color consistency is desirable.

Optionally, a monitor (not shown) can be used for displaying images of and additional information about the golf balls as they are inspected, and also for interfacing with analyzer 18. The image of the last inspected product may be displayed on the monitor so that operators may see the results of the inspection analysis, particularly if a defective golf ball has been detected. Highlights and color error markers can be set to emphasize important features or problems in the image displayed on the monitor. A freeze frame feature may be provided to freeze a defect on the screen of the monitor for close scrutiny while inspection continues. Such a feature also permits the image to be stored and displayed so that the operator may view the areas found defective by analyzer 18 while allowing the inspection process to continue. The frozen image remains displayed for an amount of time specified by the operator or until manually reset.

Thus, analyzer 18 can monitor the manufacturing process (including output quality), automatically track the production process, and generate statistics such as the total acceptable and defective products. Furthermore, when information is collected on a specific number of previously inspected golf balls, the information may be used to track the overall production quality, thereby providing information to a technician or line manager regarding the current state of the processing line. Additionally, analyzer 18 may be used to communicate production and status reports directly to an operator or to a host computer in a known manner. For example, analyzer 18 can report, such as to an operator or a programmable controller, inefficiencies such as cyclic defects, consecutive defects, percentage of defects, percentage yield, and/or forecasted yield. Because analyzer 18 can record the exact nature of a defect and also can provide a fast accurate breakdown of the types and quantities of each defect, analyzer 18 can be used to diagnose the precise problem in the processing apparatus that caused the detected defect.

Analyzer 18 may also be equipped to emit a signal or an alarm to notify the operator to review and analyze the defect image and determine what, if any, correction to the processing apparatus is necessary. Additionally, computer-generated error flags can be used to highlight defective areas of the product being inspected. This provides an immediate indication of the detected defect and the reason the golf ball was determined to be defective.

In addition to providing on-screen information and analyses, analyzer 18 may be used to generate concise, production history reports of the inspection statistics, e.g., number of defects, percentages, and production trends.

Production reports generated by analyzer 18 may include production totals or percents displaying the number of defective and acceptable products inspected, track production trends, throughput, various defect statistics, or defect results on a routine by routine basis. Such reports may be used to determine the general nature of various defects encountered in production and thereby to permit the operator/manufacturer to rectify any problems with or generally improve the system so as to result in improved production quality. Further, analyzer 18 may generate, or information provided by analyzer 18 may be used to generate, production charts graphically depicting the results, gathered over a period of time, of statistics pertaining to acceptable and defective products, relevant to overall production and/or individual production processes.

In addition to analyzing at least one characteristic of the golf ball being viewed, automated analyzer 18 also generates an analysis signal to affect the processing of the golf ball being inspected. Preferably, such signal is sent to a diversion device 28, as shown in FIG. 1, which performs a specified task based on the results of the analysis performed by analyzer 18. The specific diversion device 28 to be used depends on the process being performed on the golf ball as well as the next process to be performed. For instance, diversion device 28 may include reject and/or sorting mechanisms, programmable controllers for feedback to the production machinery, and production alarms or indicators which indicate a fundamental problem in the production equipment.

In one embodiment, a time delay for a controlled duration depending on production speed and station set-up, e.g., the distance between imager 16 and a diversion device 28, is implemented both between detection (by inspection system 10) and analysis (by analyzer 18) and between analysis (by analyzer 18) and analysis signal communication (to diversion device 28) to insure that the appropriate golf ball is acted upon.

A position detector may be used to determine the position of the golf ball between automated inspection system 10 and diversion device 28 so that the appropriate inspected golf ball is acted upon by diversion device 28. Any position detector known in the art, such as a detector determining absolute position, may be used. Means for determining and monitoring the velocity of the assembly line may also be provided to ensure further accuracy in determining the position of the golf ball to be acted upon. For example, a tach encoder may be useful in determining production rate for comparison with the analysis rate with which analyzer 18 may operate effectively. Alternatively, analyzer 18 may be appropriately programmed to send a signal to diversion device 28 at the appropriate time as determined by the production line speed and the spacing from the individual detecting apparatuses 36. In a preferred embodiment, a computer processor is utilized to track each ball as it passes through process station 10. The computer processor sends a signal to a particular processing station to indicate the particular ball which has arrived at the processing station 10 so that the process appropriate to that particular ball may be performed. The computer processor may be provided in any form desired, as known to those of ordinary skill in the art. For example, a programmable logic controller ("PLC") could communicate with analyzer 18 to track each ball. Each ball also or alternatively may be tracked by a computer to which signals from analyzer 18 are transmitted.

Diversion device 28 may perform any desired action on a golf ball which has been inspected by inspection system 12. For example, diversion device 28 may be a reject device which rejects any golf ball inspection system 12 has determined does not meet production standards. Alternatively, diversion device 28 may be a transfer device which transfers the inspected golf ball depending on conformance or nonconformance with production standards, such as a lever activated by a control signal to divert defective balls from further processing. Thus, a ball that does not meet production standards is removed, in any desired manner and at any desired time after inspection. Each golf ball that has undergone inspection by inspection system 12 may be transferred or conveyed to additional apparatus for further processing.

Referring again to FIG. 1, additional preferred features of automated inspection system 10 are shown. A product sensor 13 may also be included to trigger the inspection and analysis process. Product sensor 13 is used to prevent extraneous information (such as a scan of an empty space without a golf ball) from being transmitted and analyzed by analyzer 18 so that statistics on acceptable and defective golf balls being scanned will not be skewed. Product sensor 13 may be any desired sensor, such as an optical or magnetic sensor that detects the presence of an object within range of the imager 16, a fiber optic through beam product sensor which transmits a signal upon the passing of an object across its beam, a photoelectric eye, or a proximity switch.

Because the different features of a golf ball to be analyzed may not be readily viewed by a commercially available imager 16 because of certain viewing or environmental conditions, particularly if under ambient conditions, various environment modification devices may be provided to modify inspection conditions and thereby facilitate capturing the image of golf ball 12 by imager 16. As described in greater detail below, environment modification device 14 may, for example, include a custom lighting system which alters the lighting conditions so that visual features of the exterior surface of the golf ball or a substance applied to the exterior surface of the golf ball can be properly detected by imager 16. In one embodiment, environment modification device 14 utilizes a plurality of LEDs in different colors to achieve greater and more intense illumination of golf ball 12, such as for facilitating inspection of printed matter on the surface of golf ball 12. In that case, the LED colors are red, green, and blue so that in combination a white light is produced. More preferably, however, environment modification device 14 is a fluorescent circular illuminator that provides uniform lighting of golf ball 12. An appropriate environment modification device 14 is Model 10 CFVI High-Frequency Illuminator available from StockerYale of Salem, N.H. Additionally, a light screen 26 is preferably placed behind golf ball 12. Light screen 26 enhances the overall brightness of the environmental conditions and helps to eliminate shadows on golf ball 12. Optionally, a filter or series of filters 15 may be included between imager 16 and light source 14 or golf ball 12 to enhance the image.

Figure 6:
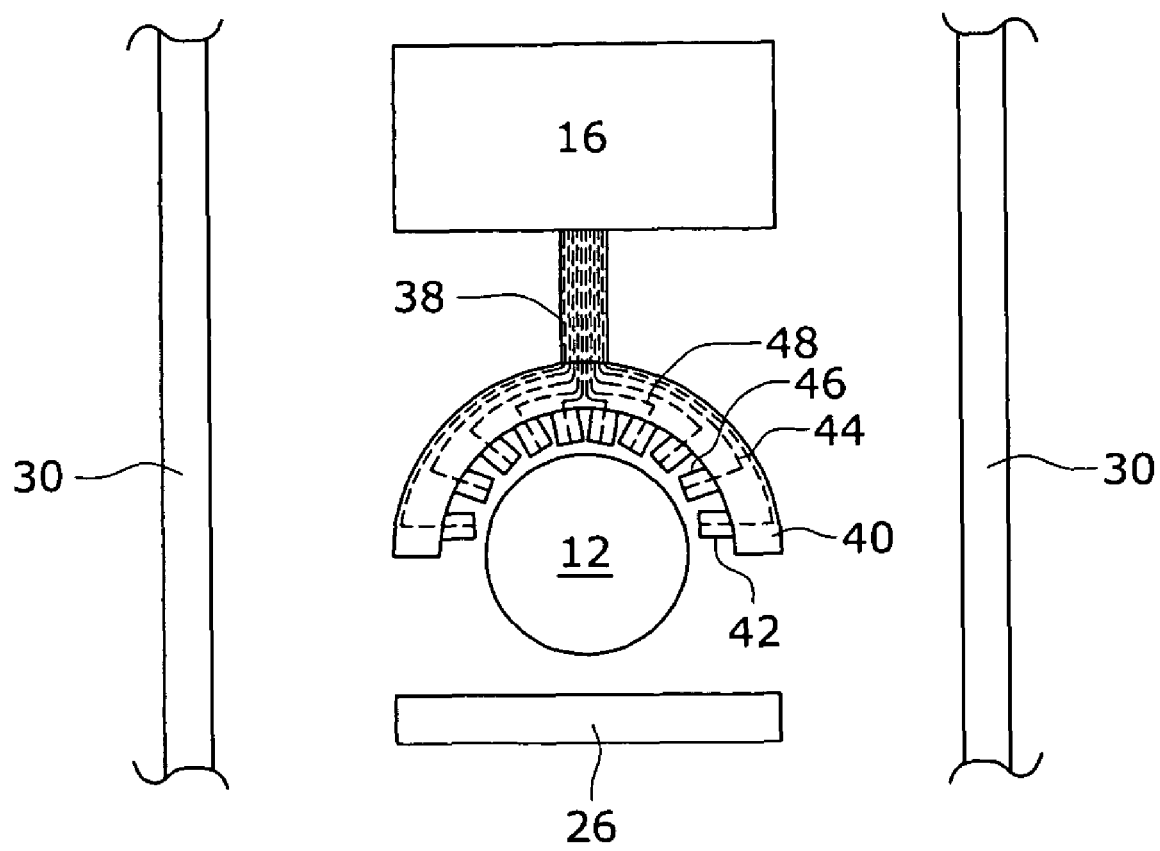
FIG. 6 is a schematic top view of an alternate vision inspection system according to the present invention.

In another embodiment, the lighting and imaging elements may be included in a fiber optic bundle 38, as shown in FIG. 6. Fiber optic bundle 38 may incorporate illumination fibers 44 or imaging fibers 48. Preferably, fiber optic bundle 38 contains both illumination fibers 44 and imaging fibers 48. Fiber optic bundle 38 is preferably connected on one end to imager 16 and on the other end to a rack 40.

Imager 16 may be any type of imager known in the art that includes fiber optic lenses or is capable of being adapted to include fiber optic lenses, for example a CCD sensor having a fiber optic lens or "snake" attached thereto. These types of imagers are known for use in endoscopic surgery, for example. While fiber optic bundle 38 contains at least one lens, or imaging fiber 48, the total number of lenses in fiber optic bundle 38 will vary, depending upon the resolution desired. In the present invention, imaging fiber 48 may comprise a single individual fiber or a group of fibers. Additionally, imager 16 also preferably includes a light source, so that at least one of the fibers or fiber groups in fiber bundle 38 is an illumination fiber 44.

Rack 40 surrounds at least a portion of golf ball 12. Although rack 40 may have any shape, preferably, rack 40 is semi-circular so that the curvature of rack 40 generally follows the curvature of golf ball 12. In one embodiment, fibers 44, 48 of fiber optic bundle 38 are fed into rack 40, where the individual fibers are separated so that each fiber 44, 48 leads to one of several ports 42, 46 disposed along an inner surface of rack 40. In another embodiment, rack 40 includes a channel to carry the fibers to ports 42, 46. Illumination ports 42 contain illumination fibers 44, and imaging ports 46 contain imaging fibers 48. Illumination fiber 44 transfers light from the light source to the surface of golf ball 12 and imaging fiber 48 transmits light information from golf ball 12 to the sensor, where the information is converted into a digital signature or pixel.

Each port 42, 46 is preferably oriented so that the surface of golf ball 12 is perpendicular to the port. Also, preferably, the ports alternate along rack 40, so that each illumination port 42 has only imaging ports 46 adjacent thereto. In this fashion, each imaging fiber 48 is receiving an image illuminated by its neighboring fibers 44 so that shadows are minimized and color appears more consistent.

Riser 34 and ball holder 20 are preferably mounted within a system support frame 30. System support frame 30 is then attached to a support surface 32, such as a floor, via several supports 22. Anti-vibration mounts 24 are preferably used to affix supports 22 to support surface 32, so that a clear image of golf ball 12 may be obtained even if support surface 32 is shaken, such as by the operation of processing equipment.

As will be appreciated, in accordance with the principles of the present invention, the above-described inspection system 10 as described above may be used in any of the various processing stations through which a golf ball is passed during manufacture. Because each processing station performs a different process, inspection system 10 may be modified to account for the specific nature of the process being performed. For instance, processes which involve printing on or coating or painting of the golf ball will require analysis of the surface characteristics, but not necessarily the shape or contour, of the ball. In contrast, processes which involve the shaping or forming of a layer of the golf ball will require analysis of the shape or contour of the ball.

While it is apparent that the illustrative embodiments of the invention disclosed herein fulfill the preferred embodiments of the present invention, it is appreciated that numerous modifications and other embodiments may be devised by those skilled in the art. Examples of such modifications include slight variations of the numerical values discussed above. Hence, the numerical values stated above and claimed below specifically include those values and the values that are approximately or nearly close to the stated and claimed values. Therefore, it will be understood that the appended claims are intended to cover all such modifications and embodiments, which would come within the spirit and scope of the present invention.

We claim:

1. A method for inspecting a golf ball having a cover material coated with a primer coat in an automated manufacturing system comprising the steps of:
    (i) aligning the golf ball, the golf ball having a cover material coated with a primer coat and an outer paint layer, the outer paint layer overlying the primer coat, wherein the primer coat and outer paint layer have unique colors, with a spectral imager;
    (ii) obtaining a spectral image of at least a portion of the golf ball which has been coated with the primer coat and outer paint layer;
    (iii) analyzing the spectral image to determine whether or not the primer coat has been applied uniformly over the cover material; and
    (iv) acting on the golf ball.

2. The method of claim 1, wherein the spectral imager comprises an area-scanning camera attached to a spectrograph and further comprising the steps of
    (v) capturing a single line of the golf ball as the spectral image;
    (vi) rotating the golf ball;
    (vii) sequentially capturing additional lines of the golf ball; and
    (viii) packing the captured lines to form at least a partial three-dimensional spectral image of the golf ball.

3. The method of claim 2, wherein the vertical axis of the three-dimensional object represents the spectrum.

4. The method of claim 1, wherein the golf ball is analyzed using a pattern matching technique.

5. The method of claim 1, wherein the golf ball is analyzed using threshold analysis.

6. The method of claim 1, wherein step (iv) comprises diverting the golf ball, sending the golf ball to a corrective processing station, or allowing the golf ball to advance to a new processing station.

7. The method of claim 1, wherein the primer coat is white and the cover material is any color other than white.

8. The method of claim 7, wherein the cover material is treated to have any color other than white.

9. The method of claim 1, wherein the spectral image is in color.

10. The method of claim 1, wherein the spectral image is in grayscale.

11. The method of claim 1, wherein the cover material is a urethane layer.

12. The method of claim 11, wherein small areas of insufficient coverage of primer coat are detected.

13. The method of claim 1, wherein the spectral imager includes a fiber optic bundle.

14. The method of claim 13, wherein the fiber optic bundle comprises at least one imaging fiber connected to a sensor.

15. The method of claim 14, wherein the imaging fiber extends to the golf ball, and wherein a free end of the imaging fiber is oriented perpendicular to the surface of the golf ball.

16. The method of claim 13, wherein the fiber optic bundle comprises at least one illuminating fiber connected to light source.

17. The method of claim 16, wherein the illuminating fiber extends to the golf ball, and wherein a free end of the illuminating fiber is oriented perpendicular to the surface of the golf ball.

* * * * *